United States Patent [19]
Behan et al.

[11] Patent Number: 5,190,915
[45] Date of Patent: Mar. 2, 1993

[54] PERFUMED STRUCTURED EMULSION IN PERSONAL PRODUCTS

[75] Inventors: John M. Behan, Kennington; Jeremy N. Ness, Canterbury; Keith D. Perring, Ashford; William M. Smith, Folkstone, all of Great Britain

[73] Assignee: Unilever Patent Holdings B.V., Rotterdam

[21] Appl. No.: 726,407

[22] Filed: Jul. 10, 1991

[30] Foreign Application Priority Data

Jul. 11, 1990 [EP] European Pat. Off. ........ 90307588.5

[51] Int. Cl.$^5$ .............................................. A61K 7/46
[52] U.S. Cl. ........................................ 512/2; 424/49; 424/65; 424/70; 424/71
[58] Field of Search ................ 512/2; 424/70, 71, 49, 424/65

[56] References Cited

U.S. PATENT DOCUMENTS

| | | | |
|---|---|---|---|
| 4,097,403 | 6/1978 | Tsutsumi | 424/450 |
| 4,115,314 | 9/1978 | Oppenlaender et al. | 512/5 |
| 4,170,655 | 10/1979 | Zeidler et al. | 512/2 |
| 4,171,455 | 10/1979 | Tomita et al. | 512/2 |
| 4,184,985 | 1/1980 | Scheuermann et al. | 512/2 |
| 4,217,344 | 8/1980 | Vanlerberghe | 424/450 |
| 4,299,737 | 11/1981 | Meffert et al. | 512/2 |
| 4,324,703 | 4/1982 | Selder | 512/2 |
| 4,508,703 | 4/1985 | Redziniak | 424/94 |
| 4,536,324 | 8/1985 | Fujiwara | 252/311 |
| 4,670,185 | 6/1987 | Fujiwara | 424/450 |
| 4,772,471 | 9/1988 | Vanlerberghe | 424/450 |
| 4,830,857 | 5/1989 | Handjani | 424/450 |
| 4,897,308 | 1/1990 | Vanlerberghe | 424/59 |
| 4,942,038 | 7/1990 | Wallach | 424/450 |
| 5,021,200 | 6/1991 | Vanlerberghe | 264/4.3 |
| 5,041,283 | 8/1991 | Kita | 424/68 |
| 5,079,227 | 1/1992 | Handjani et al. | 512/3 |

FOREIGN PATENT DOCUMENTS

| | | | |
|---|---|---|---|
| 0217105 | 4/1987 | European Pat. Off. | |
| 0316726 | 5/1989 | European Pat. Off. | 424/450 |
| WO9001921 | 3/1990 | European Pat. Off. | 424/450 |
| 1439244 | 6/1976 | United Kingdom. | |

OTHER PUBLICATIONS

Chemical Abstracts, vol. 104, 1986, p. 302, 104:10406s.
Database WPI(L), AN=78-59474A [33], Derwent Publications Ltd., London, GB, AB=J53079043 (Abstract).
Database WPI(L), AN=89-066015 [09], Derwent Publications Ltd., London, GB, AB=J01019004 (Abstract).
Lockheed et al, Cosmetics & Toiletries, vol. 101, pp. 125-137 (Nov., 1986).
Database WPI(L)/Derwent, Derwent Publications Ltd., London, GB; DD-A-239 116.

*Primary Examiner*—James H. Reamer
*Attorney, Agent, or Firm*—Cushman, Darby & Cushman

[57] ABSTRACT

The invention concerns a process for incorporating a perfume into a personal product, wherein the perfume is first combined with one or more non-ionic emulsifiers and an aqueous phase to form a structured emulsion containing liquid crystal structures, which surround the dispersed perfume, and thereafter this structured emulsion is dispersed into a personal product base. The invention also concerns the personal products thus obtained and the structured emulsions used in the process. The structured emulsions comprise 1-30% by weight of one or more non-ionic emulsifiers, 1-50% by weight of a perfume and 20-98% by weight of an aqueous phase. Preferably low shear mixing is used in preparing the emulsions.

16 Claims, 2 Drawing Sheets

PERFUMED STRUCTURED EMULSION IN PERSONAL PRODUCTS

FIELD OF THE INVENTION

The present invention concerns a process for incorporating perfumes into personal products. More specifically, the invention concerns the use of structured emulsions as vehicles for the incorporation of perfumes into personal products, resulting in products with enhanced perfume performance. The invention also concerns structured emulsions containing a perfume and personal products comprising such structured emulsions.

BACKGROUND OF THE INVENTION

The addition of perfumes to consumer products is well established, particularly for products such as household cleansers, laundry products and personal cleaning and cosmetic products. Normally, the perfume is simply admixed with the other components of the product to produce a homogeneous product but in some cases this process may be facilitated by the use of a solubiliser, such as a emulsifier or co-solvent, to disperse the perfume more readily into the product. Whilst in general the perfume does not contribute to the functional performance of the product it does serve to improve its aesthetic appeal by imparting a pleasing odour to the product both on storage and in use. Additionally it may impart a pleasing odour to substrates on which the product is used, such as skin and hair.

Where a perfume is added to a product the nature of the product can affect its performance in a number of ways. For example, the components of the product may chemically interact with the perfume; the performance of the perfume may be hindered by interactions with component(s) of the product and this may affect both its perception in the package and in use; the longevity of the perfume may be affected. Various methods are known in the art to address these problems. One approach to optimising perfume performance in products is to empirically tailor the perfume by selecting those ingredients which are known in the art to perform well in particular products. In some cases, this can severely constrain creativity in designing a suitable perfume and may have increased cost implications for the successful perfuming of a product. In another approach, encapsulation technology can be used to stop or hinder adverse interactions between perfume and product components or to allow tailored release i.e. to control the release profile. Well-known examples of such encapsulation or controlled delivery technology include processes and products described in EP 303 461 (Unilever), U.S. Pat. No. 3,516,941 (Minnesota Mining & Manufacturing Corp.), EP 332 175 (Lion Corp.), U.S. Pat. No. 4,842,761 (IFF Inc.), EP 334 666 (Union Camp Corp.), GB 2,141,730 (Colgate-Palmolive Co.), EP 332 259 and EP 332 260 (both Procter and Gamble Inc.). Often these methods result in an appreciable on-cost for the perfuming of products.

It is known that liquid crystalline phases can help to stabilise skin cream emulsions (G. Dahms in "Cosmetics and Toiletries" Vol. 101 no. 11 (1986), pp. 113–115) and they are claimed to offer advantages in moisture retention on the skin. In a similar way liquid crystalline phases can be used to form vesicles and in recent years there has been extensive literature describing the preparation and application of such vesicles known as "liposomes". Bioemulsifiers, such as phospholipids (e.g. lecithin), have been the principal materials used in the preparation of such liposomes and are being increasingly exploited in a variety of personal products, which are claimed to offer exceptional benefits as skin moisturizers, e.g. as described in EP 120 722 (Parfums Christian Dior), U.S. Pat. No. 4,508,703 (Parfums Christian Dior), U.S. Pat. No. 3,957,971 (Lever Bros. Co.). Additionally, some non-ionic emulsifiers have also been used to form liposomes with similar benefits being claimed, see U.S. Pat. No. 4,217,344 (L'Oreal), U.S. Pat. No. 4,670,185 (Lion Corp.). In WO 88/06883 (Micro Vesicular Systems) paucilamellar vesicles are suggested for a number of applications in the medical and therapeutic field. A method of preparing multilamellar lipid vesicles using certain non-ionic emulsifiers and a sterol is disclosed in WO 88/06882 (Micro Vesicular Systems). A similar method wherein hydrophilic and amphiphilic components are encapsulated in such vesicles is disclosed in WO 88/06881 (Micro-pak Inc.). In EP 347 306 compositions with high perfume concentration are described which appear to contain separate bubbles of non-ionic emulsifier (based on polyglycerol derivatives) and droplets of perfume, surrounded by a continuous aqueous phase. GB 1,439,244 describes liquid crystalline compositions prepared by mixing an aqueous phase containing an amphotheric surfactant with an organic liquid. This liquid, which may contain perfumery materials, must itself be capable of forming the required liquid crystalline structure in combination with the aqueous phase. However, the organic liquid does not appear to be surrounded, and thus protected, by the liquid crystal structures. The compositions are described as giving enhanced substantivity of the organic liquid to skin, hair etc, when directly applied thereto. Preferably, the aqueous phase of the compositions is acidified to a pH near the isoelectric point of the amphoteric surfactant to obtain maximum substantivity. Finally, the liquid crystalline compositions described lose their substantivity in combination with most anionic surfactants.

On the other hand, EP 217 105 describes, lamellar-type single phase liquid crystal compositions for application to the skin, comprising hydrophilic nonionic surfactants having an HLB of 10 or more, water soluble substances, an oily substance and a relatively small amount (preferably below 30%) of water. These compositions are cited to have the advantage of being easily washed of the skin with water, i.e. being the reverse of substantive.

Finally, EP 316 728 and EP 368 146 describe clear microemulsion cleaning compositions comprising anionic and nonionic surfactants, co-surfactants, perfume and water. These products are intended for removing oily and greasy soils.

However, none of these references suggests to use vesicles or liposomes or or similar structures to incorporate a perfume in a personal product so as to protect it against interaction with other components present in the product and enhance its performance.

SUMMARY OF THE INVENTION

It is an object of the invention to provide a simple and economical means of adding a perfume to a personal products thereby enhancing the performance of perfumes in personal products and separating the perfume from the product base. Such means would thus give the potential for improved stability in the product base, better sensory impact and may also provide enhanced delivery of the perfume to the target substrate. Thus, it is a further object of the invention to optimise the efficiency of perfume delivery to such substrate e.g. skin, hair and teeth, which promotes benefits referred to in the art as "substantivity" or "retentivity". In a similar way, it is a further object of the invention to provide a means of controlling perfume delivery at various stages of the use cycle of a product.

The invention provides a process for incorporating a perfume into a personal product, whereby the perfume is first combined with one or more non-ionic emulsifiers and an aqueous phase to form a structured emulsion containing liquid crystal structures, which surround the dispersed perfume, and thereafter this structured emulsion is dispersed into a personal product base, to produce a personal product with improved perfume performance. The invention also provides personal products obtainable by this process and perfume containing structured emulsions used in this process.

According to the invention the structured emulsion is produced by forming a non-aqueous phase comprising the perfume, a non-ionic emulsifier or an emulsifier mixture based on non-ionic emulsifiers, and optionally other adjuncts, which is mixed at a temperature at which the non-aqueous phase forms a homogeneous liquid; forming an aqueous phase consisting of water or an aqueous mixture containing water-soluble and/or water-dispersible materials; and finally mixing the two phases under shear conditions.

DETAILED DESCRIPTION OF THE INVENTION

Figure 1:
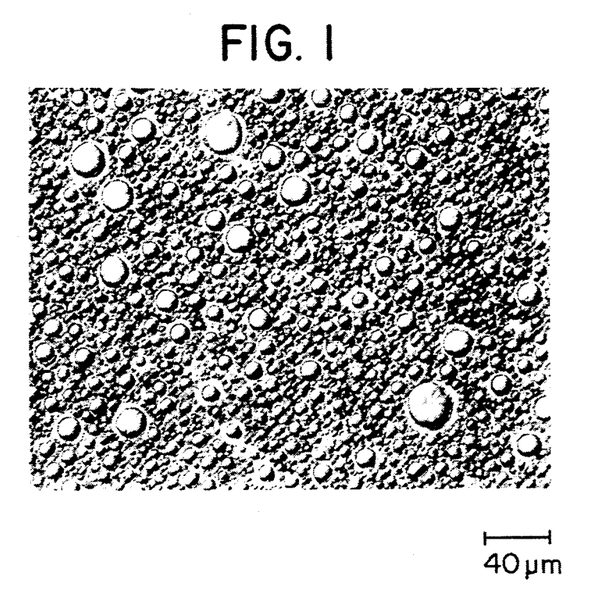
FIG. 1 is a transmitted light micrograph of the structured emulsion of example 10.
Figure 2:
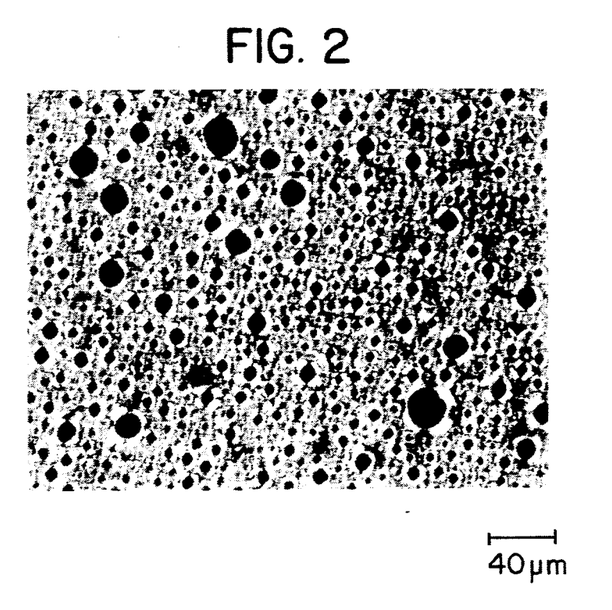
FIG. 2 is a crossed polars image of the same area as FIG. 1.
Figure 3:
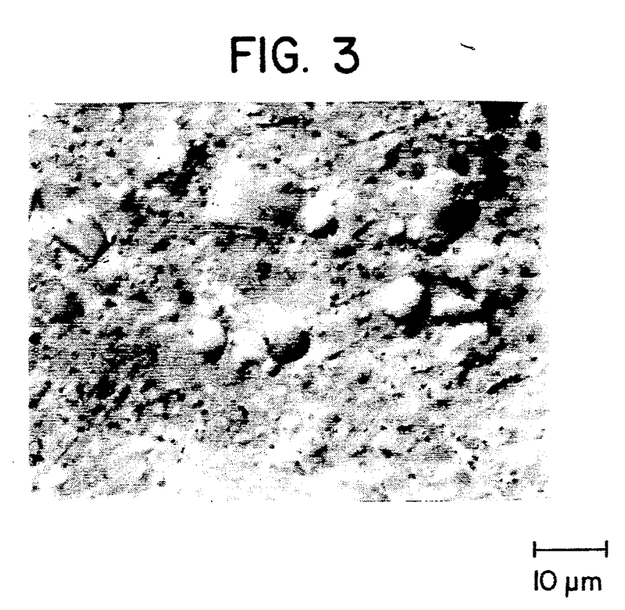
FIG. 3 is a transmitted light micrograph of the structured emulsion of example 3 dispersed in the toothpaste of example 18, illustrating the presence of droplets of perfume. Such droplets are not visible in the same toothpaste were the perfume is added neat instead of as structured emulsion.

The structured emulsions herein contain 1–50% by weight of perfume in a structured system comprised basically of one or more non-ionic emulsifiers totalling 1–30% by weight and 20–98% by weight of water or an aqueous mixture containing water-soluble and/or water-dispersible materials, hereinafter jointly referred to as "aqueous phase". Such water-soluble or water-dispersible materials may form up to 30% by weight of the aqueous phase and will hereinafter be referred to as hydrophilic adjuncts. The opaque structured emulsion system is characterised by possessing liquid crystalline layers which surround the droplets of perfume. An example of this is depicted in FIG. 1 (see below). The presence of the liquid crystalline system can be illustrated by the use of a polarising light microscope with the sample imaged between crossed polarising filters. FIG. 2 shows the classical "Maltese Cross" contrast typical of such systems (see, for example F. B. Rosevear, J. Am. oil Chemists Soc. (1954), 31 628–639).

Not all non-ionic emulsifiers will by themselves form such structured systems under the conditions of the process described here. In some cases it is advantageous or necessary to promote liquid crystal formation by the addition of structuring aids, such as up to 50% by weight relative to the non-ionic emulsifier(s) of surfactants other than non-ionics (e.g. cetyltrimethylammonium bromide (CTAB) or chloride (CTAC), sodium lauryl sulphate (SLS) sodium dodecylbenzenesulphonate, etc.), and/or up to 100% of sterols (e.g. cholesterol). Preferably the amount of structuring aids is not more than 20% by weight, more preferably 10% or less, relative to the non-ionic emulsifier(s).

Optionally, other hydrophobic adjuncts may be mixed with the perfume and thus be present in the non-aqueous phase at a total level of 0–30% by weight of the non-aqueous phase. For the purpose of this invention it is necessary that the total perfume or perfume/hydrophobic adjunct mixture is hydrophobic in nature as otherwise the emulsion will not form correctly. With the expression "hydrophobic" as used herein is meant a material which will be soluble in one or more organic solvents such as ethanol, acetone or hydrocarbon solvents and will not exhibit an appreciable degree of solubility in water. Examples of such hydrophobic materials other than perfumes include: emollients, oil-soluble polymers, sunscreens, anti-wrinkling agents, dyes, colourants, astringents, humectants, preservatives, antioxidants and conditioners.

The non-ionic emulsifiers will preferably be present in the structured emulsion at 4–25% by weight, more preferably 10–20%; the perfume (or perfume/hydrophobic adjuncts mixture) preferably at 10–50% by weight, more preferably 10–40%, particularly 20–40%; and the aqueous phase preferably at 25–86% by weight, more preferably at least 35%, particularly 40–80%. It is particularly suitable that the weight ratio of total emulsifier to perfume lies within the range 1:3 to 3:1 and the weight ratio of non-aqueous phase to aqueous phase lies within the range 1:2 to 4:3, preferably within 1:2 to 1:1. The hydrophobic and hydrophilic adjuncts may together comprise up to 30% by weight of the structured emulsion but preferably comprise no more than 20% by weight.

Non-ionic emulsifiers suitable for use in the present invention as the major liquid crystal-forming emulsifier(s) preferably have a hydrophilic-lipophilic balance (HLB) of less than 10 and are chosen from:

i.a. (Polyethoxylated) fatty alcohols of the formula:

wherein: w ranges from 0–20, preferably from 0–6, more preferably from 0–2 or 2–4; y is 0 or 1; $x+z+2y=11-23$, preferably 11–17.

i.b. Branched (polyethoxylated) fatty alcohols of the formula:

wherein: R is a branched alkyl group of 12–18 carbon atoms and w is as specified above.

ii. Glycerol mono-fatty acid esters, particularly glycerol mono-stearate, oleate, palmitate or laurate.

iii. Fatty acid esters of polyethylene glycol, particularly those of the formula:

wherein R1 is a stearoyl, lauroyl, oleoyl or palmitoyl residue; w ranges from 2–20, preferably from 2–8.

iv. Sorbitan fatty acid esters, particularly the mono- and tri-esters of the formula:

wherein: R1 is H or and R2 is and w ranges from 10–16; preferably w is 16.

v. Polyethoxylated sorbitan fatty acid esters, particularly those of the formula:

wherein: R1 is H or and R2 is u ranges from 10–16 and average (w+x+y+z) is 2–20. Preferably, u is 16 and average (w+x+y+z) is 2–4.

Particularly suitable emulsifiers are fatty alcohols as indicated under i (w=0), fatty acid diesters of polyethylene glycols as indicated under iii and the emulsifiers indicated under iv and v above.

In some cases it may be necessary to experimentally select the most suitable emulsifier from those mentioned above, or to sue mixtures of these emulsifiers. Also the use of structuring aids as mentioned above will often be helpful in obtaining a liquid crystal structure. The ability of such structuring aids to promote the formation and/or stabilisation of liquid crystals is known in the art. It is important that the non-ionic emulsifiers and structuring aids selected do not interfere with the organoleptic properties of the final product i.e. they should not impart an undesirable odour to the final product. In may cases surfactants not being non-ionics are the preferred structuring aids.

As used herein the term "perfume" denotes one or a mixture of perfume components, optionally mixed with a suitable solvent, diluent or carrier, which is used to impart a desired odour or flavour to the personal product in the package and/or in use and/or to skin or hair after use. For the purpose of this invention the term "skin" is meant to include the oral cavity.

Perfume components and mixtures thereof which can be used for the preparation of such perfumes may be natural products such as essential oils, absolutes, resinoids, resins, concretes, etc., and synthetic perfume components such as hydrocarbons, alcohols, aldehydes, ketones, ethers, acids, esters, acetals, ketals, nitriles, etc., including saturated and unsaturated compounds, aliphatic, carbocyclic and heterocyclic compounds. Examples of such perfume components are: geraniol, geranyl acetate, linalool, linalyl acetate, tetrahydrolinalool, citronellol, citronellyl acetate, dihydromyrcenol, dihydromyrcenyl acetate, tetrahydromyrcenol, terpineol, terpinyl acetate, nopol, nopyl acetate, 2-phenylethanol, 2-phenylethyl acetate, benzyl alcohol, benzyl acetate, benzyl salicylate, benzyl benzoate, styrallyl acetate, amyl salicylate, dimethylbenzylcarbinol, trichloromethylphenycarbinyl methylphenycarbinyl acetate, p-tert.butyl-cyclohexyl acetate, isononyl acetate, vetiveryl acetate, vetiverol, alpha-n-amylcinammic aldehyde, alpha-hexyl-cinammic aldehyde, 2-methyl-3-(p-tert.butylphenyl)-propanal, 2-methyl-3-(p-isopropylphenyl)propanal, 3-(p-tert.butylphenyl)propanal, tricyclodecenyl acetate, tricyclodecenyl propionate, 4-(4-hydroxy-4-methylpentyl)-3-cyclohexenecarbaldehyde, 4-(4-methyl-3-pentenyl)-3-cyclohexenecarbaldehyde, 4-acetoxy-3pentyltetrahydropyran, methyl dihydrojasmonate, 2-n-heptylcyclopentanone, 3-methyl-2-pentylcyclopentanone, n-decanal, n-dodecanal, 9-decenol-1, phenoxyethyl isobutyrate, phenylacetaldehyde dimethyl acetal, phenylacetaldehyde diethyl acetal, geranonitrile, citronellonitrile, cedryl acetate, 3-isocamphylcyclohexanol, cedryl methyl ether, isolongifolanone, aubepine nitrile, aubepine, heliotropine, coumarin, eugenol, vanillin, diphenyl oxide, hydroxycitronellal, ionones, methyl ionones, isomethyl ionones, irones, cis-3-hexenol and esters thereof, indane musk fragrances, tetralin musk fragrances, isochroman musk fragrances, macrocyclic ketones, macrolactone musk fragrances, ethylene brassylate, aromatic nitro-musk fragrances. Suitable solvents, diluents or carriers for perfumes as mentioned above are for example: ethanol, isopropanol, diethylene glycol monoethyl ether, dipropylene glycol, diethyl phthalate, triethyl citrate, etc.

In addition to the components described above, hydrophilic adjuncts may also be present in the structured emulsion at a level of 0–30% by weight of the aqueous phase, according to the nature of the product to which the perfume is to be added. Examples of such materials are abrasives, colours, dyes, preservatives, bleaches, optical brighteners, thickeners, emollients, conditioners, water-soluble polymers, water-dispersible polymers, clarifiers, pearlescent agents, salts, therapeutic agents, structurants, stabilizers, water-soluble perfumes, organic solvents.

The structured emulsions described herein can be formed under a variety of conditions, according to the particular emulsifiers chosen and the perfume to be emulsified. In general, the method of manufacture consists of separately forming the non-aqueous phase and the aqueous phase and then mixing the two phases under shearing conditions to form the final emulsion and continuing to mix while bringing the mixture to ambient temperature (if necessary). The mixing process is rapid in most cases, but for more viscous products (i.e. high emulsifier levels or viscous perfumes) it may be necessary to mix slowly or over an extended period to produce a homogeneous emulsion. The non-aqueous phase consists of the perfume (or perfume/hydrophobic adjuncts mixture), emulsifier (mixture) and optional structuring aid, and is mixed at a temperature at which it forms a homogeneous liquid, wherein "homogeneous" is defined as the absence of discrete solid particles or droplets of liquid in the non-aqueous phase. The aqueous phase, optionally containing up to 30% by weight of hydrophilic adjuncts, is preferably brought to substantially the same temperature as the non-aqueous phase before mixing the two phases. In this connection "substantially the same temperature" is intended to mean such temperature that after mixing the complete emulsion has a temperature at which the non-aqueous phase would have formed a homogeneous liquid. Low temperature processing may thus be possible for those non-ionic emulsifiers or emulsifier mixtures that are liquid at room temperature. In many cases the order of mixing the two phases is not critical, although normally the non-aqueous phase is added to the aqueous phase. In addition, although the shear rate used for mixing will affect to some extent the ultimate droplet size of the emulsion, the actual shear rate used is not critical in most cases for formation of the emulsion. Use of too high a shear rate with relatively viscous emulsions can result in destabilization of the emulsion system. The emulsions of the invention are suitably prepared under conditions of low shear, using mixers providing shear rates within the range of $10-1400\ s^{-1}$ Preferred shear rates lie within the range of $15-500\ s^{-1}$ which values are considerably lower than those provided by high shear mixers/homogenizers such as Microfluidisers (trademark of Microfluidics Corp.). Suitable information on shear rates and fluid behaviour in mixing vessels can be found in Perry's Chemical Engineer's Handbook, sixth edition, D. Green (editor), McGraw-Hill, 1984. Thus, although both high and low shear rate mixers can be used, low shear rate mixers are generally preferred (even laboratory magnetic stirrers are suitable), so obviating the need for complicated and expensive equipment and improving the economics of the process. For the examples described below, the droplets will have diameters typically lying in the range of 0.2-50 $\mu m$, with the majority of them (on a weight basis) having a droplet size above 1 $\mu m$. The resulting emulsion is opaque.

Addition of the structured emulsion to a personal product base to form the final personal product can be accomplished in a number of ways. Although it is preferable to add the emulsion at the final stage of product manufacture, it is possible in some cases to incorporate it at an intermediate stage. If an intermediate stage involves the mixing of the structured emulsion with a high concentration of a solvent (e.g. alcohols) for the non-ionic emulsifier(s), then there is a possibility that some or all of the structure may be lost. In those cases were significant loss of structure reduces or removes the benefit of the structured emulsion, then it is necessary to add the emulsion at the final stage.

In addition, it is preferred to add the emulsion to the personal product base at or about ambient temperature. Higher temperatures may be used but this is usually not necessary and may result in loss of perfume (or particular perfume components) through evaporation. In general, mixing is continued until the emulsion is evenly dispersed through the product (typically 5-30 minutes—depending on the scale of the operation and the particular emulsion/product base). In the case of solid products, it may not be possible to achieve a completely homogeneous dispersion of the emulsion through the product, but this will not adversely affect perfume performance. Mixing is preferably carried out under low shear conditions.

The personal products according to the invention are products used for personal cosmetic functions and comprise products intended for such uses as hair conditioning, skin moisturization and cleaning of teeth. Examples of such products are: toothpastes, hair conditioners, hair gels, cold wave lotions, skin creams, hand and body lotions, body deodorants, mouth washes, etc. They are characterized by possessing a low level of surfactant, typically between 0 and 4% by weight and usually less than 2.5% (not including the surfactant added with the perfume structured emulsion). Furthermore, personal products according to the invention generally comprise 0.15-99.9% by weight of water, 0.05-30% of perfume, preferably less than 5%, and a relatively large weight fraction (up to 75%) of other functional ingredients such as abrasives, preservatives, colours, dyes, bleaches, optical brighteners, thickeners, emollients, conditioners, clarifiers, pearlescent agents, salts, therapeutic agents, structurants, stabilizers, solvents and co-solvents. The total of these ingredients in a personal product with the exception of perfume is hereinafter referred to as "personal product base". Apart from the perfume added to this personal product base as a structured emulsion according to the invention, the product may also contain a quantity of perfume added in the conventional way.

The exact composition of the personal products according to the invention naturally depends on the type of product and outlines of such compositions for some products are presented below:

Thus, hair conditioners will generally comprise: 0.5-10% by weight of fatty materials/gloss agents, e.g. mineral oil, silicones and cetostearyl alcohol; 0.5-3% of emulsifier, e.g. sodium lauryl ether sulphate and ethoxylated alcohols; 0-2% of cationic conditioning agents, e.g. quaternary ammonium salts; 0-5% of polyols, e.g. propylene glycol; 0-1.5% of additional adjuncts such as anti-oxidants, preservatives and dyes; 0.05-1% of perfume; 78.5-98% of water.

Cold wave lotions generally comprise: 5-15% by weight of ammonium thioglycolate; 0.2-0.6% of ammonium hydroxyde; 0-5% of ammonium bicarbonate; 0-4% of emulsifiers, e.g. sorbitan monooleate; 0.1-2% of adjuncts such as opacifiers, chelating agents and perfume; 72-95% of water.

Toothpastes will generally comprise: 15-50% by weight of particulate matter as fillers/abrasives/thickeners, e.g. alumina, dicalcium phosphate dihydrate and calcium carbonate, and 15-15% of polyhydric humectants, e.g. glycerol and sorbitol, such that the weight fraction of particulate mater and humectants together is 55-75%; 0.5-2.5% of detergent, e.g. sodium lauryl sulphate; 0.5-2% of binding agent, e.g. carboxymethylcelluloses and gums; 0-1.5% of dental actives, e.g. sodium monofluorophosphate and anti-gingivitis agents, 1-3% of adjuncts such as sweeteners, perfume, colouring matter, preservative; 26-43% of water.

Skin creams generally comprise: 4-15% by weight of emulsifier, e.g. alkyl phosphate esters, fatty alcohols, triethanolamine soaps and fatty acid monoglycerides, 10-65% of emollient/lubricant oils, liquid paraffins and fatty materials such as almond oil, jojoba oil, lanolin, squalane, isopropyl myristate and petroleum jelly; 0-10% of humectants, particularly glycerol and other polyhydric alcohols; 0-1% of adjuncts such as stabilizers and preservatives; perfume; 20-86% of water.

Anti-perspirant emulsions generally comprise: 5-20% by weight of anti-perspirant actives, e.g. aluminium zirconium tetrachlorhydrex gly; 0-20% of lubricants, e.g. mineral oil and silicones; 0-20% of alcohols and polyols; 0-10% of emulsifiers, e.g. ethoxylated fatty alcohols; 0.5-3% of adjuncts such as perfume, preservatives, thickeners; 20-94.5% of water.

The structured emulsions when dispersed in the personal product base can be shown by visible light microscopy to give an appreciable proportion of perfume contained in discrete multilayered vesicles. Generally this proportion is 10% by weight or more of the total amount of perfume present, preferably it is 35% or more. The vesicles preferably are in the size range of from 0.5 μm upwards.

EXAMPLES

I. Structured Emulsions

Examples of emulsions produced according to the process described in this patent are given in table 1. They were produced by the following method:

i. A non-aqueous phase P is formed by mixing the following components:
A: one or more non-ionic emulsifiers;
B: a perfume according to one of the recipes A, B, C, D or E;
C: optionally one or more structuring aids; whilst maintaining the temperature of the phase P at a sufficiently high level to obtain a homogeneous liquid.

ii. An aqueous phase Q is formed, consisting of water optionally containing one or more hydrophilic adjuncts and brought at substantially the same temperature as phase P;

iii. The phases P and Q are mixed and brought to room temperature whilst continuing to mix.

Perfumes according to the following recipes were used in the structured emulsion examples mentioned in Table 1:

|  | % |
|---|---|
| Perfume A |  |
| Coumarin | 0.5 |
| Benzyl acetate extra | 4.0 |
| Benzyl salicylate | 10.0 |
| Dihydromyrcenol | 10.0 |
| Citronellol | 10.0 |
| Methyl cedryl ketone | 8.0 |
| Methyl dihydrojasmonate | 5.0 |
| 2-Phenylethanol | 10.0 |
| 5-Acetyl-3-isopropyl-1,1,2,6-tetramethylindane | 7.5 |
| Jasmopyrane forte | 10.0 |
| Linalool | 10.0 |
| Alpha-hexylcinnamic aldehyde | 8.0 |
| Isolongifolanone | 3.0 |
| Styrallyl acetate | 1.0 |
| Methylionone | 3.0 |
| Perfume B |  |
| 1,3,4,6,7,8-hexahydro-4,6,6,7,8,8-hexamethylcyclopenta(g)-2-benzopyran | 7.50 |
| Methyl cedryl ketone | 12.00 |
| Lilial | 7.00 |
| Benzyl salicylate | 7.20 |
| Alpha-hexylcinnamic aldehyde | 13.00 |
| Methyl dihydrojasmonate | 14.60 |

-continued

|  | % |
|---|---|
| 2-Phenylethanol | 9.00 |
| Dipropylene glycol | 18.00 |
| Litsea cubeba oil | 5.00 |
| Coumarin | 0.06 |
| Linalool | 3.60 |
| Hexyl salicylate | 3.04 |
| Perfume C |  |
| Benzyl salicylate | 6.5 |
| P-tert.butylanisole | 5.0 |
| Hexyl salicylate | 4.5 |
| P-tert.butylcyclohexyl acetate | 12.0 |
| O-tert.butylcyclohexyl acetate | 3.5 |
| 4-Acetoxy-3-pentyltetrahydropyran | 8.5 |
| 2-Phenylethanol | 7.5 |
| Phenylethyl acetate | 0.5 |
| Alpha-hexylcinnamic aldehyde | 5.0 |
| 2,4-dimethyl-3-cyclohexene-1-carboxaldehyde | 1.5 |
| Methyl cedryl ketone | 5.0 |
| 5-Acetyl-3-isopropyl-1,1,2,6-tetramethylindane | 2.0 |
| 2-Hexyl-2-cyclopentenone | 3.3 |
| Coumarin | 2.0 |
| Hexyl benzoate | 6.7 |
| Ethyl cinnamate | 1.5 |
| Diethyl phthalate | 15.0 |
| Perfume D |  |
| Cineole | 15.0 |
| Borneol | 10.0 |
| Cedar wood oil | 18.0 |
| Clove terpenes | 2.0 |
| Pine oil American | 10.0 |
| Diphenyl oxide | 1.0 |
| Tetrahydrolinalool | 6.0 |
| Fenchyl acetate | 5.0 |
| Benzyl benzoate | 15.0 |
| Isobornyl acetate | 18.0 |
| Perfume E |  |
| Anethole | 7.05 |
| Carvone Laevo | 8.90 |
| Menthol Laevo | 10.00 |
| Peppermint oil American | 23.00 |
| Spearmint oil American | 51.00 |
| Vanillin | 0.05 |

TABLE 1

| | Examples of emulsion systems | | | |
| Example no. | Phase P | | | Phase Q |
| | A | B | C | |
|---|---|---|---|---|
| 1 | Brij 52 5.00 g | Perfume A 5.00 g | | Water 20.0 g |
| 2 | Brij 52 4.50 g | Perfume A 5.00 g | CTAB 0.50 g | Water 20.0 g |
| 3 | Arlacel 129 5.00 g | Perfume E 5.00 g | | Water, 20.0 g, Saccharin 0.05 g |
| 4 | Arlacel 129 10.0 g | Perfume E 50.0 g | Cholesterol 1.50 g | Water 200 g |
| 5 | Span 20 8.00 g | Perfume C 40.0 g | | Water 160 g |
| 6 | Cithrol 2MO 15.0 g | Perfume D 45.0 g | CTAB 1.0 g | Water 300 g |
| 7 | Brij 30 1.00 g | Perfume A 3.00 g | CTAC 0.15 g | Water 10.0 g |
| 8 | Brij 72, 12.0 g, 721 6.0 g | Perfume A 27.0 g | | Water 80.0 g |
| 9 | Brij 58, 8.0 g Cetyl alcohol 12.0 g | Perfume C 20.0 g | | Water 60.0 g |
| 10 | Span 60 20.0 g | Perfume E 15.0 g | CTAB 2.00 g | Water 65.0 g |
| 11 | Brij 52 7.0 g | Perfume A 23.0 g | | Water 50.0 g |

TABLE 1-continued

| Example no. | Examples of emulsion systems | | | |
|---|---|---|---|---|
| | Phase P | | | |
| | A | B | C | Phase Q |
| 12 | Brij 52 7.0 g | Perfume B 23.0 g | | Water 30.0 g |
| 13 | Tween 61 15.0 g | Perfume C 17.0 g | SLS 1.50 g | Water, 65.0 g, Dye 0.05 g |
| 14 | Tween 60, 4.0 g, 61 10.0 g | Perfume B 15.0 g | CTAB, 1.00 g Cholesterol 1.00 g | Water, 60.0 g, Preserv. 0.30 g |
| 15 | Brij 52, 20.0 g, 58 5.0 g | Perfume D 36.0 g | | Water 130 g |
| 16 | Brij 30 20.0 g | Perfume A 10.0 g | | Water 70.0 g |
| 17 | Empilan KM20, 2.0 g Laurex CS 4.0 g | Perfume B 10.0 g | | Water 14.0 g |

Key to table 1:
Brij, Arlacel, Span and Tween are trademarks of ICI Speciality Chemicals.
Cithrol is a trademark of Croda Chemicals Ltd.
Empilan and Laurex are trademarks of Albright & Wilson Ltd.
CTAC = Cetyltrimethylammonium chloride.
CTAB = Cetyltrimethylammonium bromide.
SLS = Sodium lauryl sulphate

II. Personal products

The following products were prepared by the addition of the indicated structures emulsion system, made up as above, to the product base under mild mixing conditions (ambient temperature, low shear).

EXAMPLE 18

Toothpaste

| | g |
|---|---|
| Phase A: | |
| Sorbitol (70% aq) | 30.00 |
| Sodium Monofluorophosphate | 0.85 |
| Water | 38.95 |
| Phase B: | |
| Syloblanc 81 (silica)(1) | 20.00 |
| Sodium Carboxymethylcellulose | 1.60 |
| Titanium Dioxide | 0.50 |
| Phase C: | |
| Sorbitol (70% aq) | 5.00 |
| NaOH (50% aq) | 0.40 |
| Empicol LXV(2) | 1.50 |
| Saccharin | 0.20 |
| Phase D: | |
| Structured emulsion of example 3 | 1.00 |

(1) W. R. Grace and Co.
(2) Albright and Wilson

Phase B was mixed thoroughly with Phase A for thirty minutes under high shear conditions. Phase C was then stirred into this mixture under vacuum, maintaining the temperature at 40° C. Finally, phase D was added and mixed under low shear for fifteen minutes.

The test toothpaste (T1) was evaluated in comparison with a control paste (T2), prepared according to the above procedure and containing the same perfume F at the same level, but added as neat perfume instead of structured emulsion. To this end samples of both toothpastes were stored in glass jars at ambient temperature for ten days. The samples were then assessed for flavour impact by a panel of six flavourists/evaluators during normal brushing of teeth for 2 minutes. The test sample T1 was found by all the panellists to give significantly higher impact than the control T2, as is indicated by the rank sum analysis of the test results given in table 2.

TABLE 2

| Sensory assessment of toothpastes | | | | | | | |
|---|---|---|---|---|---|---|---|
| | Ranking (flavour intensity) | | | | | | |
| | Assessor | | | | | | |
| Toothpaste | A | B | C | D | E | F | Sum |
| T1 | 1 | 1 | 1 | 1 | 1 | 1 | 6 |
| T2 | 2 | 2 | 2 | 2 | 2 | 2 | 12 |

Ranking: 1 = best, 2 = worst.

EXAMPLE 19

Hair Conditioner

| | g |
|---|---|
| Phase A: | |
| Crodex N(1) | 2.00 |
| Arlacel 165(2) | 1.00 |
| Cetyl alcohol | 1.50 |
| Phase B: | |
| Polyquart H81(3) | 1.00 |
| Crotein C(2) | 0.50 |
| D-Panthenol(4) | 2.00 |
| Citric Acid | 0.20 |
| Polymer JR 30M(5) | 0.45 |
| Purified water | to 100.00 |
| Phase C: | |
| Preservative | q.s. |
| Phase D: | |
| Structured emulsion of example 2 | 0.50 |

(1) Croda Chemicals Ltd.
(2) ICI Speciality Chemicals
(3) Henkel Chemicals Ltd.
(4) Hoffmann La Roche
(5) Union Carbide Corp.

Phase A was heated to 70° C. and phase B to 75° C. Phase B was then added to phase A with rapid stirring, avoiding aeration. Phase C and D were added after cooling to ambient.

EXAMPLE 20

Cold Wave Lotion

| | g |
|---|---|
| Phase A: | |
| Ammonium Thioglycollate (40% aq) | 23.3 |
| Purified water | 73.3 |
| Ammonia 0.880 S.G. | 0.70 |
| Ammonium Bicarbonate | 2.00 |
| Phase B: | |
| Structured emulsion of example 11 | 0.70 |

The ammonium thioglycollate was stirred into the water and the amonia slowly and carefully added to the mixture, followed by the ammonium bicarbonate. After this mixture had cooled to ambient the perfume was added.

EXAMPLE 21

Skin Cream

| | g |
|---|---|
| Phase A: | |
| Empilan KM20(1) | 1.80 |

-continued

|  | g |
|---|---|
| Laurex CS(1) | 7.20 |
| White Petroleum Jelly | 15.00 |
| Light Mineral Oil | 6.00 |
| Phase B: | |
| Preservative | q.s. |
| Purified water | 69.8 |
| Phase C: | |
| Structured emulsion of example 17 | 0.20 |

(1) Albright and Wilson Ltd.

Phases A and B were heated separately to 70° C. B was then mixed into A with constant stirring and stirring was continued until the cream was cooled to ambient. The perfume (phase C) was then stirred into the cool product.

EXAMPLE 22

Skin Cream

|  | g |
|---|---|
| Phase A: | |
| Emulgin B1(1) | 3.00 |
| Eutanol G(1) | 22.00 |
| Iso-Propyl Myristate | 5.00 |
| Glycerol mono-stearate (non self-emulsifying) | 15.00 |
| Phase B: | |
| Hygroplex HHG(1) | 3.00 |
| Preservative | q.s. |
| Purified Water | 51.8 |
| Phase C: | |
| Structured emulsion of example 12 | 0.20 |

(1) Henkel Chemicals Ltd.

Phases A and B were heated separately to 70° C. B was then mixed into A with constant stirring and stirring was continued until the cream was cooled to ambient. The perfume was then stirred into the cool product.

We claim:

1. A process for incorporating a perfume into a personal product, which comprises first combining the perfume with one or more non-ionic emulsifiers and an aqueous phase to form a structured emulsion containing liquid crystal structures, which surround the dispersed perfume, and thereafter dispersing this structured emulsion into a personal product base, wherein the structured emulsion comprises 1-30% by weight of one or more non-ionic emulsifiers, 1-50% by weight of a perfume and 20-98% by weight of an aqueous phase, and the non-ionic emulsifiers are chosen from the group consisting of:

i.a. (Polyethoxylated) fatty alcohols of the formula:

$R_3-(O-CH_2)_x-(CH=CH)_y-(CH_2)_z-(O-CH_2-CH_2)_w-OH$ wherein: w ranges from 0-20; y is 0 or 1; $x+z+2y=11-23$;

i.b. Branched (polyethoxylated) fatty alcohols of the formula:

$R-(O-CH_2-CH_2)_w-OH$ wherein: R is a branched alkyl group of 12-18 carbon atoms w is as specified above;

ii. Glycerol mono-fatty acid esters;

iii. Fatty acid esters of polyethylene glycols of the formula:

$R_1-(O-CH_2-CH_2)_w-OH$ or $R_1-(O-CH_2-CH_2)_w-O-R_1$ wherein R1 is a stearoyl, lauroyl, oleoyl or palmitoyl residue; w ranges from 2-20;

iv. Sorbitan fatty acid mono- and tri-esters of the formula:

$$\text{HO}\diagup\diagdown\text{OR1}$$
$$\diagdown_O\diagup\text{CHOR1}$$
$$\phantom{xxxxxx}|$$
$$\phantom{xxxxxx}\text{CH}_2\text{OR2}$$

wherein: R1 is H or $-\underset{\underset{O}{\|}}{C}-(CH_2)_{w'}-CH_3$ and R2 is $-\underset{\underset{O}{\|}}{C}-(CH_2)_{w'}-CH_3$ and w ranges from 10-16;

v. Polyethoxylated sorbitan fatty acid esters, particularly those of the formula:

$$\phantom{x}\diagup(O-CH_2-CH_2)_w-OH$$
$$O\phantom{xx}$$
$$\phantom{x}\diagdown(O-CH_2-CH_2)_x-OR1$$
$$CH-(O-CH_2-CH_2)_y-OR1$$
$$|$$
$$CH_2-(O-CH_2-CH_2)_z-OR2$$

wherein: R1 is H or $-\underset{\underset{O}{\|}}{C}-(CH_2)_u-CH_3$ and R2 is $-\underset{\underset{O}{\|}}{C}-(CH_2)_u-CH_3$ u ranges from 10-16 and $(w+x+y+z)$ is 2-20.

2. A process according to claim 1 wherein the structured emulsion additionally comprises one or more structuring aids chosen from surfactants not being non-ionics in an amount of 0-50% and/or sterols in an amount of 0-100% by weight of the non-ionic emulsifier(s).

3. A process according to claim 2 wherein the structuring aids are surfactants selected from the group consisting of cetyltrimethyl-ammonium bromide, cetyltrimethly-ammonium chloride, sodium lauryl sulphate, sodium dodecylbenzenesulphonate, and the sterol is cholesterol.

4. A process according to claim 1 wherein the perfume contains hydrophobic adjuncts in an amount of 0-30% by weight of the no-aqueous phase.

5. A process according to claim 1 wherein the aqueous phase contains hydrophilic adjuncts in an amount of 0-30% by weight of the aqueous phase.

6. A process according to claim 1 wherein the structured emulsion is prepared by:
   (a) forming a non-aqueous phase consisting of the perfume, the optional hydrophobic adjuncts, the non-ionic emulsifier or emulsifier mixture and the optional structuring aids, wherein the structuring aids are selected from surfactants other than non-ionics and from sterols, by mixing at a temperature at which the non-aqueous phase forms a homogeneous liquid;
   (b) forming an aqueous phase consisting of water and the optional hydrophilic adjuncts and bringing this to substantially the same temperature as the non-aqueous phase;
   (c) mixing the two phases under shear conditions.

7. A process according to claim 6 wherein the two phases forming the structured emulsion are mixed under low shear.

8. A process according to claim 1 wherein the structured emulsion comprises 4-25% by weight of non-ionic emulsifier(s), 10-50% of perfume and 25-86% of aqueous phase and the weight ratio of total emulsifier, including optional structuring aids, to perfume lies within the range 1:3 to 3:1 and the weight ration of non-aqueous phase to aqueous phase lies within the range 1:2 to about 4:3.

9. A process according to claim 1 wherein the structured emulsion is added to a personal product base so as to produce a personal product comprising 0-4% by weight of surfactant, 0.15-99.9% of water, 0.05-30% of perfume and 0-75% by weight of one or more functional ingredients chosen from: abrasives, colours, dyes, preservatives, bleaches, optical brighteners, thickeners, emollients, conditioners, clarifiers, sunscreen agents, pearlescent agents, salts, therapeutic agents, structurants, stabilizers, solvents and co-solvents.

10. A process according to claim 9 wherein the personal product made is a hair conditioner.

11. A process according to claim 9 wherein the personal product made is hair gel.

12. A process according to claim 9 wherein the personal product made is a cold wave lotion.

13. A process according to claim 9 wherein the personal product made is a tooth paste.

14. A process according to claim 9 wherein the personal product made is a skin cream.

15. A process according to claim 9 wherein the personal product made is body lotion.

16. A process according to claim 9 wherein the personal product made is a body deodorant.

* * * * *

UNITED STATES PATENT AND TRADEMARK OFFICE
CERTIFICATE OF CORRECTION

PATENT NO. : 5,190,915
DATED : March 2, 1993
INVENTOR(S) : BEHAN et al.

It is certified that error appears in the above-identified patent and that said Letters Patent is hereby corrected as shown below:

Column 13, line 54 "R3—(O—CH2)x—(CH=CHOy—CH2-" to
--CH$_3$—(CH2)x—(CH=CHOy—CH2---

Column 14, line 68, change "no-aqueous" to
--non-aqueous--

Signed and Sealed this

Fourth Day of January, 1994

Attest:

BRUCE LEHMAN

Attesting Officer     Commissioner of Patents and Trademarks